United States Patent [19]

Ohashi et al.

[11] Patent Number: 5,585,354
[45] Date of Patent: Dec. 17, 1996

[54] SUPPRESSANT OF CORNEAL SUBEPITHELIAL CLOUDING

[75] Inventors: Yuichi Ohashi; Keizo Takahashi, both of Ehime-ken, Japan

[73] Assignee: Suntory Limited, Osaka, Japan

[21] Appl. No.: 404,150

[22] Filed: Mar. 14, 1995

[30] Foreign Application Priority Data

Apr. 18, 1994 [JP] Japan ................................ 6-078541

[51] Int. Cl.$^6$ ............................................... A61K 37/00
[52] U.S. Cl. ................................................. 514/12; 514/912
[58] Field of Search ........................................ 514/12, 912

[56] References Cited

PUBLICATIONS

Transcriptional Control of Human Diploid Fibroblast Collagen Synthesis By γ–Interferon, Biochemical and Biophysical Research Communication, vol. 123, No. 1, Aug. 30, 1984 pp. 365–372.

Molecular Cloning of Human Immune Interferon cDNA and its Expression in Eukaryotic Cells, Nucleic Acids Research, vol. 10, No. 8, 1982, pp. 2487–2501.

Expression of Human Immune Interferon cDNA in *E. coli* and Monkey Cells, Nature, Patrick W. Gray et al., vol. 295, Feb. 11, 1982, pp. 503–508.

Selective Inhibition of Human Diploid Fibroblast Collagen Synthesis by Interferons, Rapid Publication, Sergio Jimenez et al., vol. 74, Sep. 1984, pp. 1112–1116.

Gamma–Interferon Inhibits Collagen Synthesis in Vivo in the Mouse, R. D. Granstein et al., J. Clin. Invest., vol. 79, Apr. 1987, pp. 1254–1258.

*Primary Examiner*—Zohreh Fay
*Attorney, Agent, or Firm*—Cushman Darby & Cushman

[57] ABSTRACT

Suppressant of corneal subepithelial clouding, in particular, one that is capable of effective suppression of corneal subepithelial clouding which can potentially develop after superficial keratectomy with an excimer laser. The suppressant contains gamma-interferon or variants thereof as an active ingredient and it is formulated in dosage forms suitable for topical administration. In may be commonly applied as an eye drop or an ophthalmic ointment after formulation with additives such as isotonizers, buffer agents, stabilizers, antiseptics, pH modifiers and ophthalmic ointment bases.

5 Claims, No Drawings

SUPPRESSANT OF CORNEAL SUBEPITHELIAL CLOUDING

BACKGROUND OF THE INVENTION

This invention relates to a suppressant of corneal subepithelial clouding that contains γ-interferon as an active ingredient. More particularly, the invention relates to a suppressant of corneal subepithelial clouding which develops after superficial keratectomy with an excimer laser, as well as a method of suppressing the corneal subepithelial clouding.

Eye glasses and contact lenses are devices that are capable of very safe and reliable correction of myopia, hyperopia and astigmatism due to corneal ametropia. However, they suffer the serious disadvantage of the need to be worn by the user. In certain cases, it is impossible to correct errors in refraction by means of eye glasses and contact lenses.

Since S. L. Trokel et al. first proposed the ophthalmologic application of an excimer laser in 1983 (Am. J. Ophthalmol., 96: 710–715, 1983), adaptations of the excimer laser to clinical ophthalmology have been the subject of many researchers. The recent years have seen progresses in clinical studies on the use of excimer lasers in the correction of myopia and astigmatism and in the treatment of corneal superficial clouding. Superficial keratectomy (SK) using an excimer laser was first reported by O. Sordaravic et al. in 1985. Use of an excimer laser in the correction of in myopic refractive errors was tried by M. B. McDonald in 1988. Since the result was incomparable to the conventional therapies, the new approach was incorporated in a therapeutic experiment under the regulatory control of the FDA. A clinical study of Phase III started in 1991 and the monitoring of the results continues. In Europe, Seiler and his coworkers have been carrying out clinical studies since 1988. A full-fledged clinical therapeutic experiment started in 1993 in Japan (Yoshiaki Hara, Practical Ophthalmology, 178–181, 1993; Shigeru Kinoshita, Atarashii Ganka (New Aspects of Ophthalmology), 10(2): 221–224, 1993; Masakazu Yamada, Ganka (Ophthalmology), 35:347, 1993).

Superficial keratectomy using an excimer laser covers various applications of an excimer laser to the cornea and it may be classified as follows in accordance with the operative technique used (Keizo Takahashi, Practical Ophthalmology, 187–193, 1993 and Shigeru Kinoshita, Atarashii Ganka (New Aspects of Ophthalmology), 10(2): 221–224, 1993):

(1) Phototherapeutic keratectomy (PTK) which involves the ablation of corneal superficial clouding (this technique has good adaptation to cases of subepithelial clouding such as granular corneal dystrophy, lattice corneal dystrophy, gelatinous globular corneal dystrophy and zonal corneal dystrophy);

(2) Photorefractive keratectomy (PRK) which involves the correction of myopia by reducing the corneal refractive power; and (3) Astigmatic T-excision and photoastigmatic keratectomy (PAK) which are directed to the correction of corneal astigmatism.

While the utility of excimer lasers in the ophthalmologic area is being established, several problems that need solution have been pointed out. The biggest problem is corneal subepithelial clouding (shallow, diffused retiform clouding just below the epithelium) that develops at the site of laser application and which can be result in lower vision. This clouding peaks in 1–2 months after the operation and it has been postulated, but not established, that this is caused by in collagen synthesis which takes part in the healing of wounds or certain changes mucopolysaccharides. Attempts are being made to suppress the subepithelial clouding of the cornea by applying steroids to the eye. However, opinions are divided as regards the use of steroids and, considering negative points such as inadequacy of their efficacy and possible side effects, steroids are not a complete solution to the problem. Unless this problem is solved, one cannot say that all visual functions are restored and, hence, the problem that prevents clinical applications of an excimer laser to the ophthalmologic area persists and needs an effective solution.

SUMMARY OF THE INVENTION

An object, therefore, of the invention is to suppress the subepithelial clouding of the cornea.

A more specific object of the invention is to provide a pharmaceutical composition that is very effective in suppressing the subepithelial clouding of the cornea that occurs after superficial keratectomy with an excimer laser.

DETAILED DESCRIPTION OF THE INVENTION:

Gamma-interferon (IFN-γ) was first discovered by E. F. Wheelock in 1965 as an interferon-like substance that was derived from human lymphocytes and he also reported that IFN-γ had stronger cell growth suppressing and tumor control actions than the other classes of interferons. The amino acid sequence of human IFN-γ was revealed at the Second Annual International Congress for Interferon Research which was held in San Francisco, USA. October 1981. The DNA sequence of a human gene coding for that amino acid sequence was later unravelled (R. Devos et al., Nucl. Acid. Res., 10:2487, 1982 and P. W. Gray et al., Nature, 295:503, 1982). The ability of IFN-γ to suppress the growth of collagen was also reported by J. Rosenbloom and S. A. Jimenez (Biochem. Biophys. Res. Commun., 123:365, 1984 and J. Clin. Invest., 74:1112, 1984) and by R. D. Granstein et al. (J. Clin. Invest., 79:1254, 1987). Commercial grades of IFN-γ as derived from humans and various animals are available and their production has started using synthetic genes and some of them are already marketed as pharmaceuticals.

It has been postulated that collagen synthesis which is involved in the healing of wounds and certain changes in mucopolysaccharides may take part in the corneal clouding at the site of illumination with an excimer laser but this has not yet been demonstrated unequivocally to become an established theory. Therefore, the ability of IFN-γ to suppress the subepithelial clouding of the cornea which develops after superficial keratectomy with an excimer laser has not been proved prior to the accomplishment of the present invention.

Under the circumstances, the present inventors hypothesized that the cause of the clouding would have something to do with collagen formation. Combining this hypothesis with the collagen synthesis inhibiting action of IFN-γ, they applied rat IFN-γ to the eyes of rat models and studied its effect of suppressing corneal subepithelial clouding which develops after superficial keratectomy with an excimer laser. As a result, the inventors found that the rat IFN-γ not only reduced the formation of subepithelial collagen but also suppressed the clouding of the cornea. These results demonstrated the legitimacy of the hypothesis put forward by the inventors. Additionally, since it was known that human IFN-γ had the same collagen synthesis inhibiting action as rat IFN-γ, it become clear that human IFN-γ would exhibit the ability to suppress the corneal subepithelial clouding by the same mechanism of action as rat IFN-γ. The present invention has been accomplished on the basis of these findings.

The IFN-γ that can be used in the invention may be of a native or recombinant gene type but the latter type is preferred since it can be supplied consistently. The human IFN-γ reported at the Second Annual International Congress for Interferon Research, S. F. USA, October 1981 is not the only IFN-γ that can be used in the invention and its variants, as well as analogs obtainable from non-human animal are applicable as long as they are capable of suppressing the corneal subepithelial clouding which develops after superficial keratectomy by means of an excimer laser. Exemplary variants of the reported human IFN-γ include those which have one or more constituent amino acids deleted, inserted or replaced, as exemplified by the deletion of three amino acids (CysTyrCys) at N terminal and the deletion of C terminal by processing. Non-human analogs are used for specific purposes of veterinary treatments in accordance with the specific kind of the animal to be treated in such a way that the intended action will be attained.

The suppressant of corneal subepithelial clouding according to the invention is preferably administered locally, topically in the form of an ophthalmic preparation. The concentration of IFN-γ in an ophthalmic preparation may be set at levels that exhibit its therapeutic efficacy depending upon the symptom and age of the patient, as well as the severity of the corneal subepithelial clouding and the type of the applied technique of superficial keratectomy with an excimer laser. Although not intended to be limited to any particular values, the concentration of IFN-γ is preferably in the range of 0.00001–1 wt %. If eye drops are to be applied, they may be administered in one to several doses a day, each dose consisting of one to several drops, which is equivalent to a daily dose of 0.0001–0.1 mg per adult.

Exemplary ophthalmic preparations include ordinary eye drops, ophthalmic suspensions and ophthalmic solutions of dissolve-before-use type. Ophthalmic ointments and any other dosage forms may be used as long as they can be administered topically as ophthalmic drugs. To formulate pharmaceutical preparations, not only the active ingredient but also other common additives (optional) in ophthalmic preparations are mixed and formulated by known procedures. Exemplary additives include: isotonizers such as sodium chloride and potassium chloride; buffer agents such as sodium hydrogenphosphate and sodium dihydrogenphosphate; stabilizers such as disodium edetate; antiseptics such as ethylparaben, butylparaben and benzalkonium chloride; pH modifiers such as sodium hydroxide and dilute HCl; and ophthalmic ointment bases such as white petrolatum and liquid paraffin.

EXAMPLE 1

Eye Drop

| (Formula 1) | |
|---|---|
| IFN-γ | 0.001 g |
| Sodium chloride | 0.9 g |
| Sterile distilled water | To make 00 ml |

According to Formula 1 except that the concentration of IFN-γ being selected properly, various eye drops can be formulated at varying concentrations of the active ingredient.

| (Formula 2) | |
|---|---|
| IFN-γ | 0.01 g |
| Sodium chloride | 0.8 g |
| Sodium hydrogenphosphate | 0.1 g |
| Sodium dihydrogenphosphate | q.s. |
| Sterile distilled water | To make 100 ml |

According to Formula 2 except that the concentration of IFN-γ being selected properly, various eye drops can be formulated at varying concentrations of the active ingredient.

EXAMPLE 2

Ophthalmic Ointment

| (Formula 3) | |
|---|---|
| IFN-γ | 0.005 g |
| White petrolatum | 90 g |
| Liquid paraffin | To make 100 g |

According to Formula 3 except that the concentration of IFN-γ being selected properly, various ophthalmic ointments can be formulated at varying concentrations of the active ingredients.

TEST

Object:
To investigate the effectiveness of applying IFN-γ to the eye that developed corneal subepithelial clouding after superficial keratectomy with an excimer laser.
Subject:
Six BN rats (11-wk old) having 12 eyes
Method:
(1) Anesthetization: By intraperitoneal injection of Ketalar (ketamine hydrochloride, 0.42 ml)+Celactal (xylazine hydrochloride 0.07 ml)
(2) Application of excimer laser: EC-5000 (NIDEX); energy density, 144 mJ/cm$^2$; frequency, 50 Hz; beam spot, 3.0 mmφ; ablation depth, 50 μm; ablation rate, 1.0 μm/scan
(3) Right eye: Treated with Tarivid (of loxacin) ophthalmic ointment and drops of 0.9% physiological saline immediately after lasing, followed by the application of Tarivid eye drop and 0.9% physiological saline on the next day, which was repeated for one week on a four-times-a-day basis Left eye: Treated with Tarivid ophthalmic ointment and drops of 100,000 IU/ml of IFN-γ immediately after lasing, followed by the application of Tarivid eye drop and 100,000 IU/ml of IFN-γ on the next day, which was repeated for one week on a four-times-a-day basis.
(4) Rating: At the first week of the operation, the degree and the area of subepithelial clouding were rated in scores with a slit lamp microscope; a histopathological study was also conducted. The rating in scores was done by a doctor, who did not know the protocol for the test, specializing in the cornea.

RESULTS:
(1) Subepithelial clouding rated in scores

TABLE 1

|   |                  | "Area" Score | "Degree" Score | Total |
|---|------------------|--------------|----------------|-------|
| 1 | Right Eye (R.E.) | 4            | 1              | 5     |
|   | Left Eye (L.E.)  | 1            | 3              | 4     |
| 2 | R.E.             | 4            | 2              | 6     |
|   | L.E.             | 3            | 1              | 4     |
| 3 | R.E.             | 3            | 2              | 5     |
|   | L.E.             | 3            | 2              | 5     |
| 4 | R.E.             | 2            | 2              | 4     |
|   | L.E.             | 1            | 1              | 2     |
| 5 | R.E.             | 2            | 2              | 4     |
|   | L.E.             | 1            | 2              | 3     |
| 6 | R.E.             | 3            | 3              | 6     |
|   | L.E.             | 2            | 2              | 4     |

TABLE 2

|                                   | Mean "area" score | Mean "degree" score |
|-----------------------------------|-------------------|---------------------|
| Eyes treated with physiological saline | 3.0               | 2.0                 |
| Eyes treated with IFN-γ           | 1.8               | 1.8                 |

In the group of eyes treated with IFN-γ, the subepithelial clouding lessened both in "degree" and "area" scores. From a statistical viewpoint, the clouding was suppressed significantly in the "area" score but not in the "degree" score. There was also a significant difference in the total score (the sum of "area" and "degree" scores).

(2) The post-operative, subepithelial secretion of type 1 collagen was reduced.

Conclusion:

The application of IFN-γ to the eye was effective in suppressing the corneal subepithelial clouding which developed after superficial keratectomy with an excimer laser.

The invention provides a pharmaceutical composition that has high therapeutic efficacy in suppressing corneal subepithelial clouding, particularly the clouding that occurs after superficial keratectomy as applied to correct corneal ametropia by means of an excimer laser.

What is claimed is:

1. Method of suppressing corneal subepithelial clouding by topical administration of an effective dose of γ-interferon or a variant thereof.

2. Method according to claim 1 wherein γ-interferon or a variant thereof is administered as an eye drop or an ophthalmic ointment.

3. Method according to claim 1 wherein γ-interferon or a variant thereof is administered in a daily dose of 0.0001–0.1 mg.

4. A suppressant of corneal subepithelial clouding that contains γ-interferon or a variant thereof as an active ingredient.

5. A suppressant of corneal subepithelial clouding according to claim 4 which is formulated as an eye drop or an ophthalmic ointment.

* * * * *